United States Patent [19]

Clark et al.

[11] Patent Number: 4,982,432
[45] Date of Patent: Jan. 1, 1991

[54] ELECTROTACTILE VOCODER

[75] Inventors: Graeme M. Clark, Eltham; Peter J. Blamey, Mt. Waverley, both of Australia

[73] Assignee: University of Melbourne, Victoria, Australia

[21] Appl. No.: 443,857

[22] Filed: Nov. 29, 1989

Related U.S. Application Data

[63] Continuation of Ser. No. 726,262, Apr. 23, 1985, abandoned.

[30] Foreign Application Priority Data

May 30, 1984 [AU] Australia ............................... PG5281

[51] Int. Cl.$^5$ ............................................... G10L 3/02
[52] U.S. Cl. .......................................... 381/41; 381/48;
        381/49; 381/50; 340/407; 128/420.5
[58] Field of Search ...................... 381/41, 68, 48, 49,
        381/50; 340/407; 128/420.5; 434/112

[56] References Cited

U.S. PATENT DOCUMENTS

| | | | |
|---|---|---|---|
| 2,150,364 | 3/1939 | Dudley | 340/407 |
| 3,612,061 | 10/1971 | Collins | 340/407 |
| 3,831,296 | 8/1974 | Hagle | 340/407 |
| 4,390,756 | 6/1983 | Hoffmann et al. | 128/419 R |
| 4,441,202 | 4/1984 | Tong et al. | 381/68 |
| 4,581,491 | 4/1986 | Boothroyd | 340/407 |

Primary Examiner—Lawrence E. Anderson
Attorney, Agent, or Firm—Skjerven, Morrill, MacPherson, Franklin & Friel

[57] ABSTRACT

An electrotactile vocoder for persons having impaired hearing in which electrical stimulation is applied to a multiplicity of electrodes in contact with either side of each finger so as to electrically stimulate the digital nerves of the user under the control of stimulator circuitry which is in turn controlled by processing circuitry for a speech signal received by a directional microphone worn on the ear of the user. The speech processor is suitably of the type described in U.S. Pat. No. 4,441,202 Tong et al. modified to cause stimulation of the digital nerves via the eight finger electrodes and a common electrode held in contact with the wrist of the user.

6 Claims, 6 Drawing Sheets

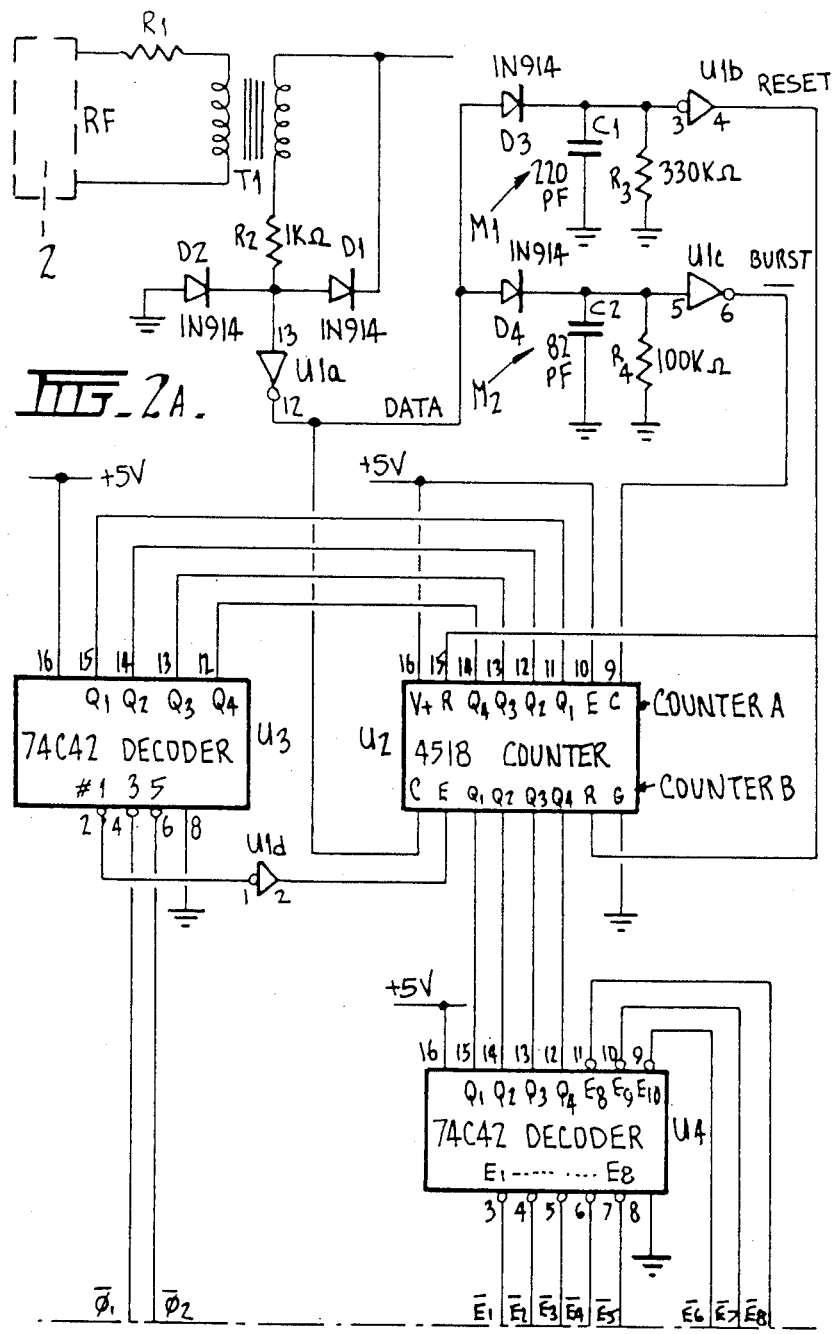
FIG_2A.

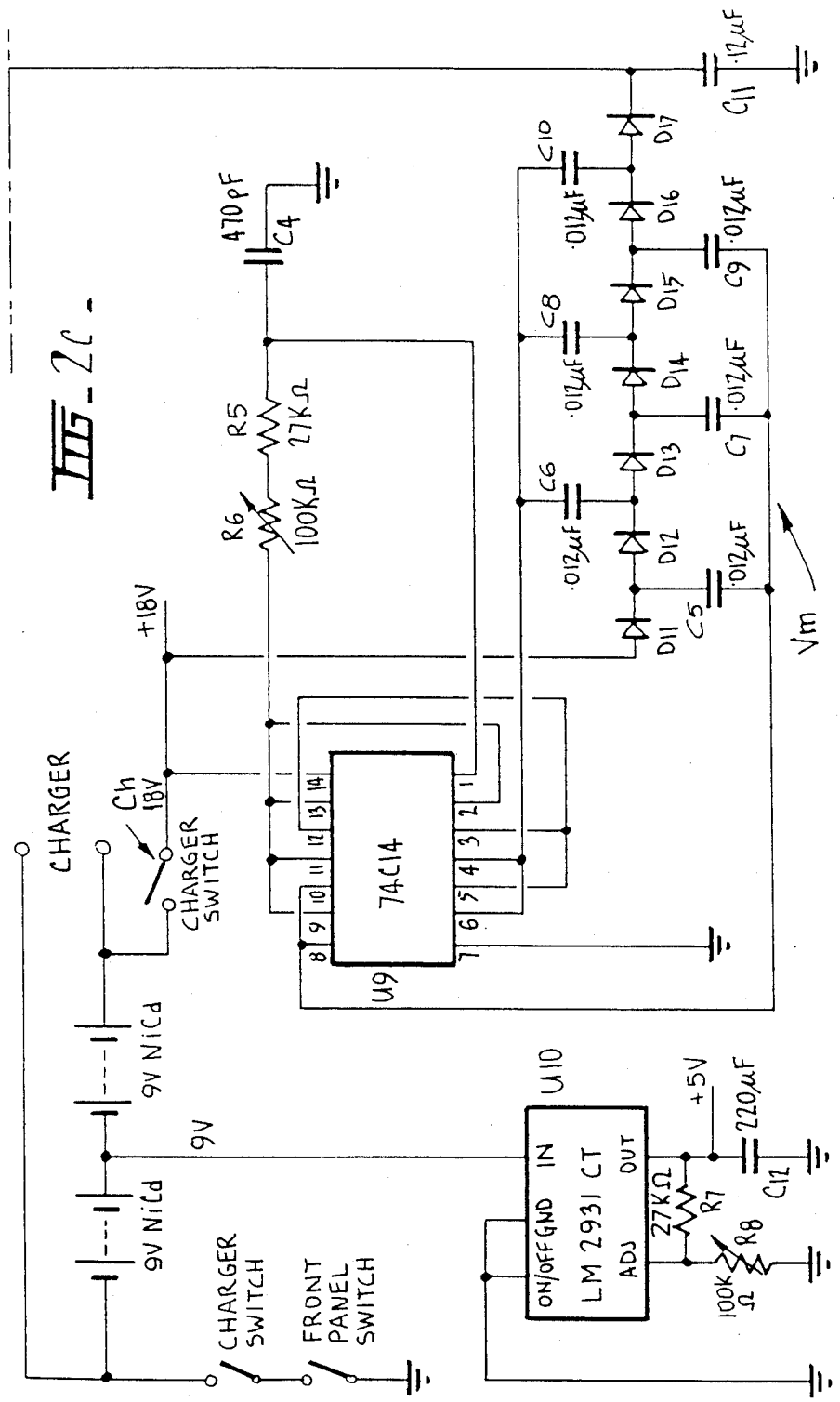
FIG_2c

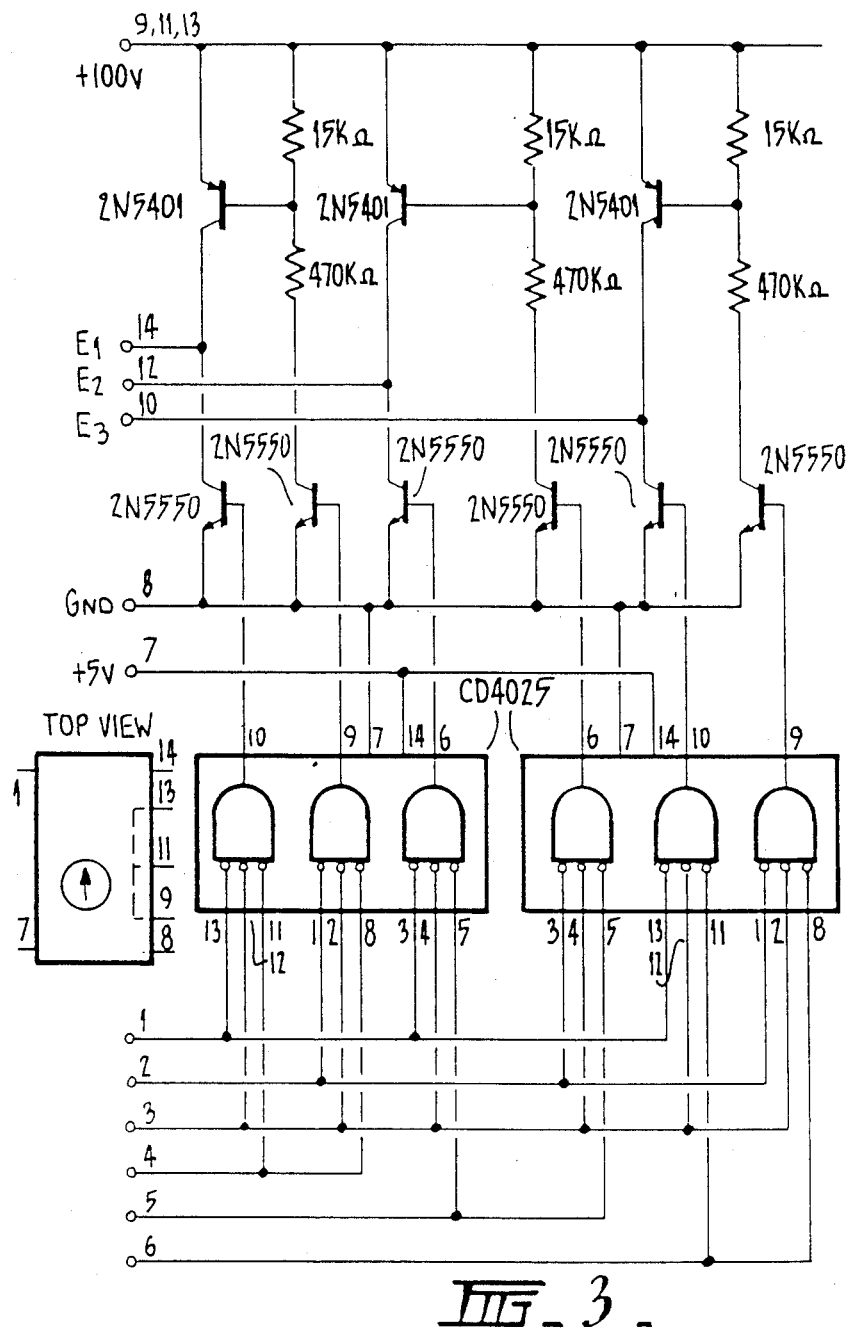
FIG_3

ELECTROTACTILE VOCODER

This application is a continuation of application Ser. No. 06/726,262, filed April 23, 1985, now abandoned.

FIELD OF THE INVENTION

This invention relates to electrotactile vocoders for persons having impaired hearing.

BACKGROUND OF THE INVENTION

A number of studies have shown that deaf patients can get help in communicating by presenting components of speech as patterns of skin stimulation.

Single channel devices have been found particularly useful in presenting the rhythm, stress and duration patterns of speech (Erber, N. P. 1978—International Journal of Rehabilitaton Research, Vol. 1 Pages 27-37 entitled "Vibratory Perception by Deaf Children"; Plant, G. L. 1979—Australian Journal of Audiology, Vol. 1 Pages 76-82 entitled "Use of Tactile Supplements in the Rehabilitation of the Deafened—a case study"; Proctor, A. 1982—Proceedings of the Second National Child Development Conference Melbourne August 1982 entitled "Effects of tactual aid on language comprehension of pre-lingual profoundly deaf children"; Plant, G. L. & Risberg, A. 1983—Speech Transmission Laboratories Quarterly Progress Report Vol. 2-3 Pages 61-84 entitled "The Transmission of Fundamental Variations via a Single Channel Vibrotactile Aid"). Multi-channel devices have been able to convey information that is especially important in identifying vowels, consonants and words (Pickett, J. M. & Pickett, B. H. 1963—Journal of Speech and Hearing Research Number 6 Pages 207-222 entitled—Communication of Speech Sounds of a Tactual Vocoder; Saunders, F. A. 1973—Proceedings in the Fourth Annual Meeting of the Bio-Medical Engineering Socieity, Los Angeles, Calif. entitled—"Electrotactile Sensory Aids for the Handicapped"; Kirman, J. H. 1974—Journal of the Acoustic Society of America Number 55 Pages 163-169 entitled—"Tactual Perception of Computer derived format deafness from voiced speech"; Engelmann, S. and Rosov, R. J. 1975—Journal of Exceptional Children Number 41 Pages 245-253 entitled—"Tactual Hearing Experiment with Deaf and Hearing Subjects; Spens, K. E. 1980—Speech Transmission Laboratories Quarterly Progress Report Number 4 Pages 23-39 entitled—"Tactile Speech Communication Aids for the Deaf"; Sparks, D. W., Kuhl, P. K., Edmonds, A. E. & Gray, G. P. 1978—Journal of the Acoustic Society of America Number 63 Pages 246-257 entitled—"Investigating the Mesa (Electrotactile Speech Aid: the transmission of segmental figures of speech); Reed, C. M., Durlach, N. I. & Braida, L. D., 1978—A.S.H.A. American Speech and Hearing Association Monograph Number 20 entitled "Research on Communication and Speech: a review"; Traunmuller, H. 1980—Journal of Communication Disorders Number 13 Pages 183-193 entitled "Sentiphone: a tactual speech communication aid"). Most tactile vocoders have stimulated the skin by mechanical vibraiton on body loci such as the forearm and the fingertips. This has been carried out by using solenoids, other electromagnetically operated units or piezo-electric devices. Electrotactile stimulation has been carried out by delivering electric current to the skin receptors and nerve endings, primarily around the abdomen but also the forearm and the fingertips.

Many of the studies have been carried out in the laboratory as they have been research based requiring the use of bench top equipment. It has been acknowledged that further progress will require more portable units that will enable studies in the field and allow the patients to learn to use them most of the time. This goal has been achieved with a single channel vibratory device (Plant) but still has not been possible for either vibratory or electrotactile multichannel skin stimulus units. Mechanical vibrators are large and have a high power consumption requiring a number of batteries. Electrotactile stimulation using an array of surface electrodes requires less power and is lightweight and compact. A problem with electrical stimulation of the skin receptors and nerve endings, however, is that the dynamic range for electric current is small and the sensation is not pleasant and frequently described as prickly. Research conducted by the applicant has confirmed the value of a simple single channel vibratory device. It has also shown that with electrical stimulation, moving patterns can be detected which have similar time courses to the frequency transitions of consonants which suggests that an appropriate unit could be helpful in understanding speech.

As a result, a stimulus unit presenting speech by electrotactile stimulation employing the electrical principles used by Saunders was constructed. In addition, two electrode arrays with matrices of $8 \times 8$ electrodes have been developed. The system can allow different speech processing strategies to be evaluated on deaf patients. Psychophysical tests have confirmed the small dynamic range between threshold and pain and have shown that some subjects experience an unpleasant prickly sensation within the operating range.

BRIEF DESCRIPTION OF THE INVENTION

It is an object of the invention to provide a stimulus unit for an electrotactile vocoder in which the above problems are at least ameliorated.

The invention provides a stimulus unit for an electrotactile vocoder comprising a multiplicity of electrodes for transmitting current pulses to the skin of the user such that the pulses are detectable by the digital nerves.

Preferably, the electrodes are adapted to be held in contact with the fingers of the hand of the user, preferably adjacent the knuckles at either side of each finger. A common electrode is preferably attached to the wrist of the user or in some other suitable position.

The current pulses are preferably low level biphasic current pulse applied in accordance with a predetermined speech coding strategy based on a speech signal received by a speech processing unit.

As a result of the above, a new approach has been taken to the problem of presenting speech as tactile stimulation. It has been discovered that charge balanced bi-phasic pulses applied to electrodes overlying the digital nerves produce sensations that have a greater dynamic range and are described by the patients as much more pleasant than electrotactile stimulation of the skin receptors and nerve endings. Psychophysical studies have also shown good performance in the discrimination of pulse rates and electrode positions.

BRIEF DESCRIPTION OF THE DRAWINGS

One preferred embodiment of the invention will now be described with reference to the accompanying drawings in which:

FIG. 3 is a circuit diagram of the hybrid circuit used in the circuit of FIG. 2.

DESCRIPTION OF THE PREFERRED EMBODIMENTS

Figure 1:
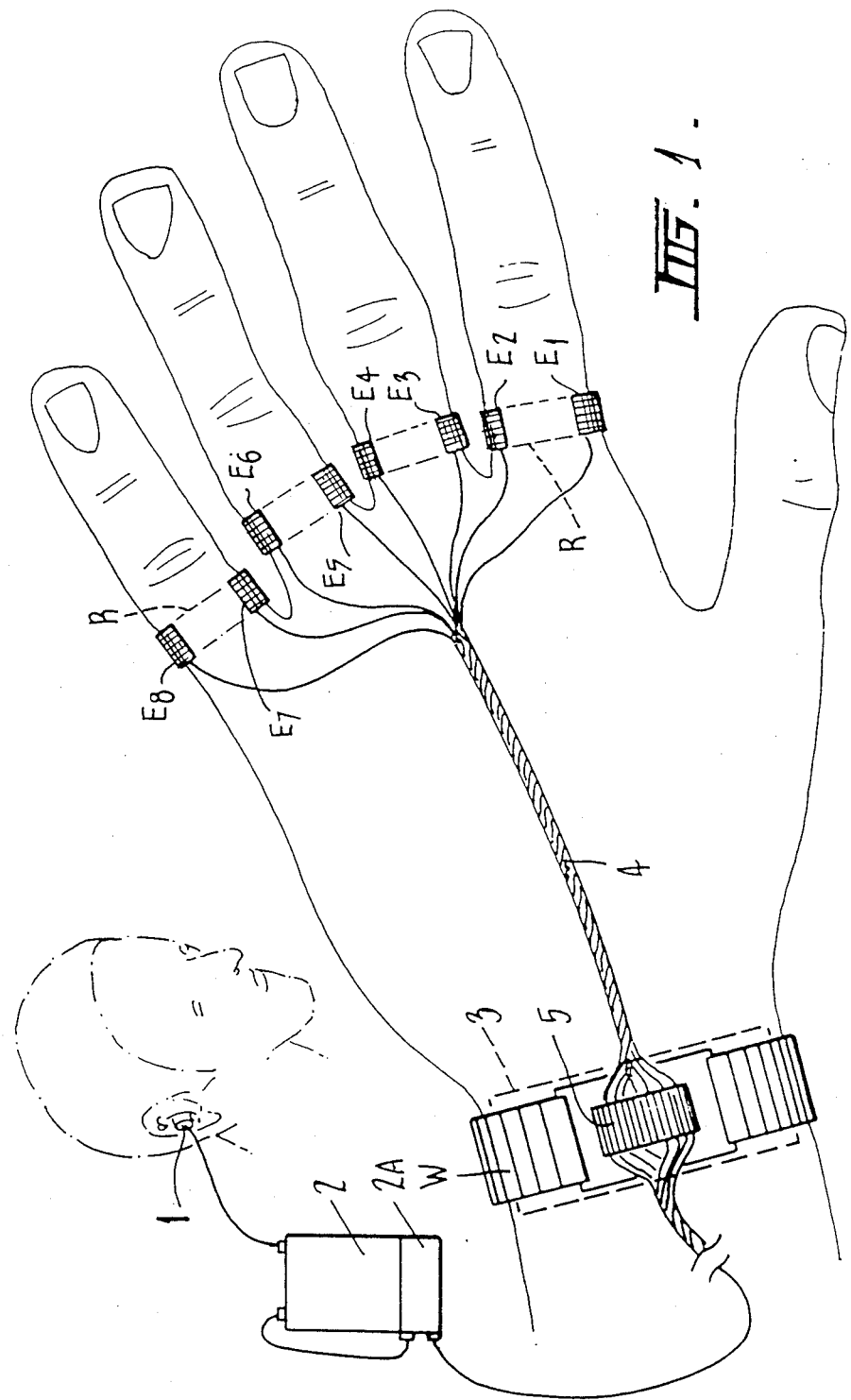
FIG. 1 is a schematic diagram of a tactile vocoder embodying the invention.

Referring firstly to FIG. 1 of the drawings, the tactile vocoder embodying the invention will be seen to comprise a directional microphone 1 worn on the ear and which discriminates in favour of sounds coming from the direction the wearer is facing, a speech processor 2 for processing the speech signal from the microphone and converting it into bursts of pulses describing where the stimulation is to be applied and for how long, and stimulus electrodes including a common electrode 3 in contact with the inside of the wrist and eight finger electrodes E1 to E8 each of which is connected by electrode leads 4 to a connector 5, mounted on a nylon watch band W for maintaining the common electrode 3 in place, and then to the speech processor 2.

The electrodes E1 to E8 are constructed from a fine grade stainless steel wire mesh and are each approximately 0.5 cm$^2$ in size and are positioned one on each side of each finger between the palm and the first knuckle. The electrodes E1 to E8 are held in position by flexible plastic rings R which allow free independent movement of the fingers while maintaining electrical contact between the electrodes E1 to E8 and the fingers. It has been found that this arrangement provides adequate electrical contact between the fingers and the electrodes without the application of electrode jelly. The common electrode 3 is similarly formed from a stainless steel wire mesh and is approximately 10 cm$^2$ in size (e.g. 5 cm×2 cm) and is held in contact with the inside of the wrist to avoid the usually hairy region on the outside of the wrist.

The speech processor 2 is a multi-channel speech processor of the type described in U.S. Pat. No. 4,441,202 Tong et al. and in Crosby, P. A., Clark, G. M., Dowell, R. C., Kuzma, J. A., Money, D. K., Patrick, J. F., Saligman, P. M. and Tong, Y. C.—Journal of Acoustic Society of America Number 74 Pages 1911-1913 entitled "The Preliminary Communication of a Channel Cochlear inplant hearing prosthesis", and Tong, Y. C., Blamey, P. J., Dowell, R. C. & Clark, G. M.—Journal of Acoustic Society of America Number 74 Pages 73-80 entitled "Psychophysical Status evaluating the feasability of a speech processing strategy for a multiple channel cochlear implant" and as manufactured by Nucleus Limited of 1 Woodcock Place, Lane Cove, 2066, New South Wales, Australia under the type number WSPI, with additional stimulator circuitry 2A which is described further below with reference to FIG. 2 of the drawings. The subject matter of this U.S. Pat. No. 4,441,202 is incorporated herein by reference. It will be noted from the above U.S. Patent that the speech processor 2 estimates the speech signal parameters which are not required in the present embodiment. For example neither the amplitude of the fundamental voicing component of the speech signal nor the determination of whether the speech signal is voiced or unvoiced is required in the present case.

The stimulator circuitry 2A produces constant-current (approximately 1.5 mA) bi-phasic stimulus pulses between the selected electrode E1 to E8 and an output connected to the common electrode 3. The two current pulse phases are separated by a fixed interval of 100uS during which no current flows. It has been found that if this interval is omitted, a greater pulse width for each phase is required to reach the same sensation level. The circuitry determines from the output of the speech processor 2 the electrode number and width of stimulus pulse between 1uS and 20uS. In the present embodiment, the width of each pulse is a compressed function of the estimated amplitude of the second formant component of the speech signal, as extracted by the speech processor 2. However, in future versions of the invention it will be preferred to base the pulse width on the estimated amplitude of the whole speech signal. The compression of the amplitude range is achieved by the automatic gain control incorporated in the speech processor 2 and by the use of a linear function that relates the logarithm of the pulse width to the logarithm of the amplitude such that the full range of the amplitude stimulated by the speech processor corresponds to the full range between threshold and comfortable level for each electrode.

Figure 2B:
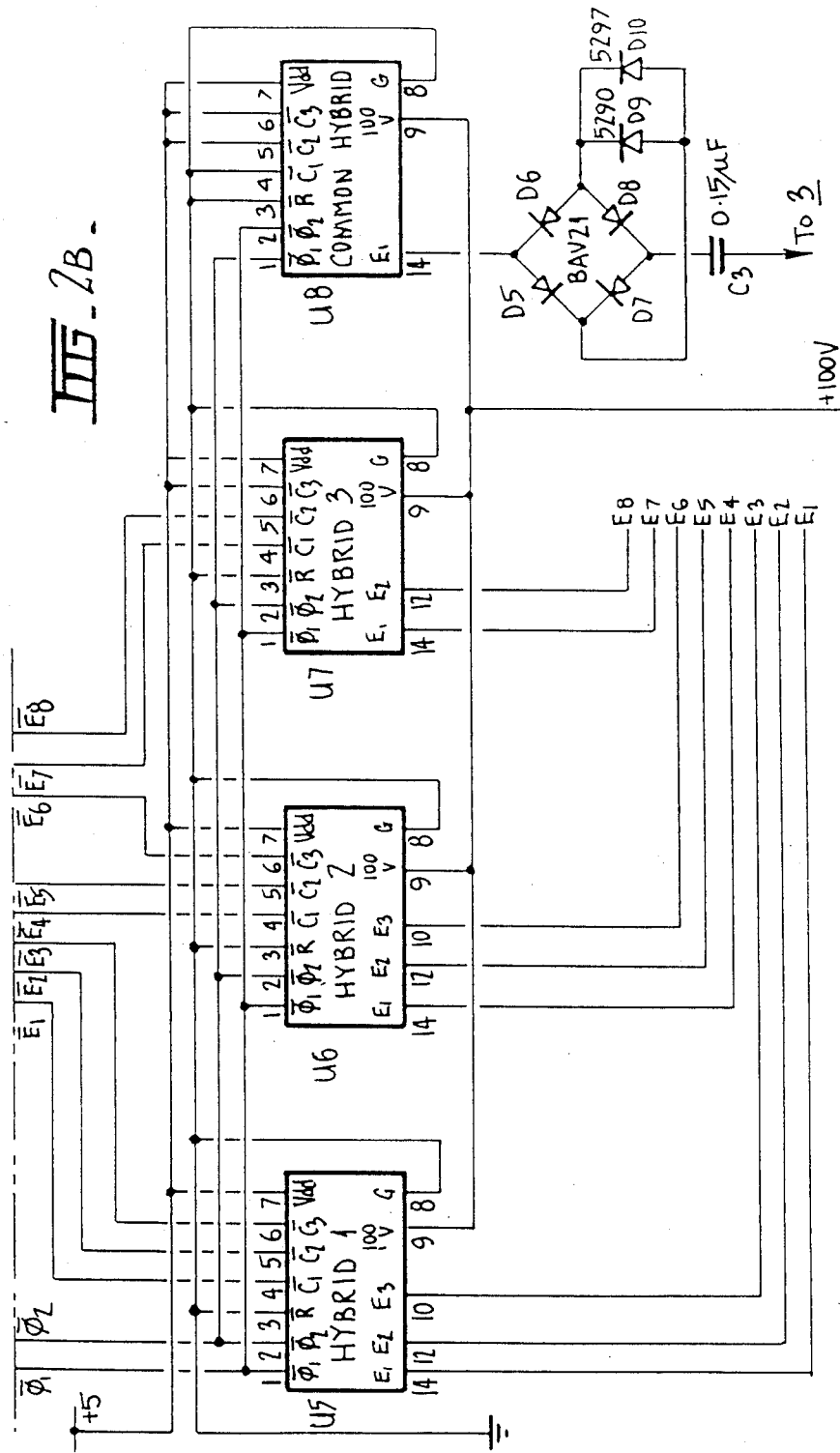
FIG. 2 is a circuit diagram of the signal processing circuitry associated with the vocoder of FIG. 1.
Figure 4:
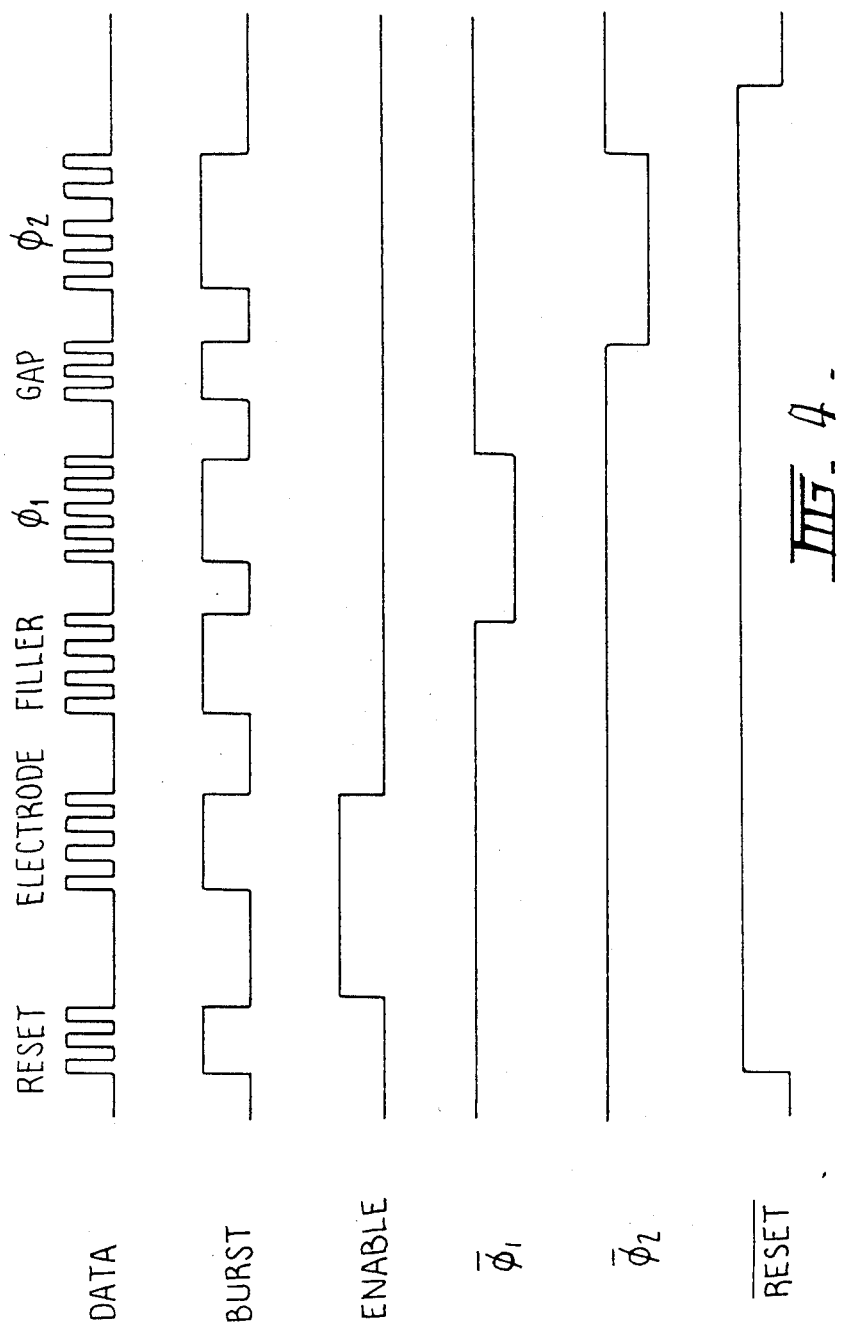
FIG. 4 shows the pulse wave forms appearing at the positions indicated in FIGS. 2 and 3.

Referring now to FIG. 2 of the drawings, the stimulator circuitry will be seen to comprise an input transformer T1 which couples the output signal from the speech processor 2 and provides electrical isolation from the speech processor and microphone, which may be in contact with the body and would otherwise form unwanted paths for the stimulus current. The information from the speech processor 2 is encoded in groups of bursts of 2.5 MHz pulses at high amplitude and resistors R1, R2 and diodes D1 and D2 and the phasing of input transformer T1 are chosen to limit the amplitude applied to inverter U1a and ensure that the first pulses are not distorted. Invertor U1a inverts the signal and restores it to a rectangular shape. The signal is at this point the "data" signal shown in FIG. 4 of the drawings. This data signal is applied to a counter B and to two monostable pulse detectors M1 and M2.

The monostable pulse detectors M1 and M2 comprise diode D3 and capacitor C1 and diode D4 and capacitor C2 respectively. When the data signal pulse is high, the diodes D3 and D4 charge the capacitors C1 and C2. Between pulses, the capacitors C1 and C2 then discharge via resistors R3 and R4. The time constant of R3 and C1 is chosen so that C1 will not discharge sufficiently during the gaps between the bursts of pulses for inverter U1b to change state. Similarly, the time constant of R4 and C2 is chosen so that C2 will be discharged within this period but not during the gaps between the pulses. In this manner, the output of inverter U1b is low during an entire group of bursts of pulses (i.e. a single stimulation) and the output of inverter U1c is low during each burst of pulses and goes high sometime between pulses. Each time the output of U1c goes high, counter A is clocked and its binary outputs are then decoded by decoder U3 to generate three control signals $\phi 1$, $\phi 2$ and enable for counter B. $\phi 1$ and $\phi 2$ are used to generate the two phases of the output pulse. In the present embodiment, the component values shown in FIG. 2 provide time constants of about 8us and 60us respectively. However, other values will be effective depending on the programming of the speech processor described blow, provided the longer time constant is about three or four times the shorter time constant and the longer time constant does not exceed about 100us.

In operation, C1 is initially discharged and the output of inverter U1b is high, holding the counters A and B in the reset state. When the first pulse of the first burst of a group of bursts arrives, C1 and C2 are both charged, counters A and B are no longer reset and counter B is inhibited from counting as counter A, and therefore the decoder U3, are still in state zero.

At the end of the first burst of pulses, C2 discharges and the output of U1c will go high, clocking counter A to state 1. Decoded by U3, the state 1 output will go low and enable counter B via the inverter U1d. When the second burst of pulses arrives, they are counted by counter B and at the end of the second burst, counter A is clocked to state 2 so that the state 1 of output of U3 goes high and counter B is disabled while leaving the count of pulses in the second burst on its outputs as a binary number. This number identifies the electrode which is to be stimulated and is decoded by decoder U4 to generate eight electrode select signals E1 to E8. The circuit continues to process incoming burst of pulses in the manner described above so that after the third burst, the state 3 output of decoder U3 goes low to generate the phase 1 ($\phi$1) signal and the phase 2 ($\phi$2) signal after the fifth burst.

The speech processor 2 controls the pulse width of the phases by changing the number of pulses in the fourth and sixth bursts and the gap between them by the number of pulses in the fifth burst. Finally, when the end of the group is reached and no more bursts arrive, C1 will discharge and the counters will again be reset.

The electrode select signals from decoder U4 and the phase select signals from decoder U3 are connected to high voltage switching circuits U5 to U8 which are implemented as hybrids of the type shown in FIG. 3 of the drawings. When both of the phase signals $\phi$1 and $\phi$2 are high, the AND gates on the hybrids keep the output transistors off and all of the electrodes E1 to E8 and 3 are open circuit. When the phase signal $\phi$1 goes low, and one of the electrode select lines to one of the hybrids U5, U6 or U7 is also low, then the corresponding output from that hybrid will be connected to common or earth. At the same time, because the phase inputs to the common hybrid U8 are reversed, its output will be connected to +100 V. Thus, the finger electrode is connected to 0 V and the common electrode 3 is connected to +100 V via diodes D5, D9, D10 and D8 and capacitor C3. Diodes D9 and D10 are current regulator diodes and capacitor C3 provides fault isolation. Similarly, when the second phase signal $\phi$2 is low, the finger electrodes are connected to +100 V and the common electrode 3 is connected to 0 V via the same circuitry. This provides a total peak-to-peak swing of 200 V to cope with high skin resistences.

The stimulator circuitry is powered by rechargable batteries from which a +5 V supply, regulated by an integrated circuit voltage regulator U10, is derived. The +100 V stimulator supply is derived from a parallel-fed Cockcroft-Walton voltage multiplier Vm. The voltage multiplier Vm is driven from a square wave oscillator U9 which generates two outputs 180° apart in phase. The frequency of operation and the component values are selected so that the high voltage will collapse if a sustained load is applied to the output, such as by a fault, which may otherwise endanger the person using the device.

Before the vocoder may be used, the "map" in the programmable read only memory of the speech processor 2 must be modified to change the stimulation levels to suit finger stimulation and to suit each user. Psychophysical investigations of stimulus patterns show wide variations of threshold and dynamic range from one subject to another and from one finger to another in each subject. Thresholds and dynamic ranges vary from day to day but within limits that are workable for the representation of speech patterns. Good discrimination of pulse width changes and pulse rate changes have been achieved with little or no training. Perfect recognition of the stimulated electrode is also immediately possible.

The setting up procedures for the speech processor 2 are carried out using a microcomputer interfaced to the speech processor in a suitable manner. As a first step, the threshold and comfortable levels of stimulation for each electrode are measured interactively with the tester raising and lowering the pulse width for a short train of pulses applied to each electrode until consistent thresholds and comforable levels are attained. It is important that comfortable levels are matched across electrodes so that changes in electrode are not confused with changes in loudness or intensity of the incoming speech signal. A procedure in which a stimulus on one electrode is matched with a stimulus on another electrode is used to check the matching.

Although the implementation of many different coding schemes for speech information would be possible on the basis of psychophysical properties so far measured, the use of the Nucleus speech processor and the similarity of the psychophysical results to those achieved in the case of the multiple-channel cochlear implant made it practical to use the same speech processing strategy in the present case. Thus, each electrode to be stimulated is selected on the basis of the frequency of the most prominant peak in the speech spectrum between 800 and 4,000 Hz, that is, the second formant frequency for vowel sounds. The pulse rate is selected to be a linear function of the fundamental frequency of the speaker's voice and the pulse width is a compressed function of the speech amplitude envelope tailored to fit the threshold and dynamic range of the electrode being stimulated.

In one suitable strategy, the second formant frequency spectrum is divided amongst the eight finger electrodes, for example, on the following basis: E1: 0-900 Hz, E2: 900-1100 Hz, E3: 1100-1300 Hz, E4: 1300-1500 Hz, E5: 1500-1700 Hz, E6: 1700-2400 Hz, E7: 2400-3300 Hz and E8: 3300-4000 Hz.

The above frequency values and the selected threshold and comfortable levels are programmed into a temporary map which can accessed by the speech processor to confirm that the map is suitable for use with continuous speech. Following confirmation, the final version of the map is programmed into the programmable read only memory in the speech processor 2 and the vocoder is then ready for use. If it is found that any one of the electrode sites is insufficiently sensitive, stimulation to that electrode may be excluded and the second formant frequency range divided amongst the remaining electrodes.

The sensations produced by the device embodying the invention are similar to those that would be experienced if a vibrating object was placed against the side of the finger. As the electrical pulse width is increased, the sensation becomes stronger and spreads towards the tip of the finger. No sensation is felt at the common electrode 3 for the usual stimulus regime. When high pulse rates and large pulse widths are used, a stinging sensation may be felt at the common electrode. This sensation occurs at lower pulse rates and shorter pulse widths when an inadequate surface area of electrode is in contact with the skin. However, it is possible to avoid this problem by adjusting the electrode placement.

What we claim is:

1. A portable electrotactile vocoder to be worn by a hearing impaired person, comprising:
    means for generating an input signal the parameters of which correspond to the features of formant frequencies, fundamental frequency and waveform amplitudes of a detected speech signal;
    means for converting said input signal into control signals, and for generating electrical pulses of predetermined width, rate and current in accordance with said control signals;
    a multiplicity of electrode means for conveying said current pulses to electrically stimulate nerve bundles located in the tissue of the hearing impaired person; and
    said current pulses having electrical parameters such that said electrical stimulation of said nerve bundles provides the user with a spatial indication of formant frequency, an indication of speech waveform amplitude magnitude and a temporal indication of fundamental frequency;
    said electrode means being positioned spatially on both sides of the four fingers of one hand of the hearing impaired person, between the palm and the proximal knuckle, and further comprising a common ground electrode applied to the wrist of the hearing impaired person, wherein the application of said electrical pulses to said finger electrode means results in electrical stimulation of the digital nerve bundles located in the tissue below each electrode.

2. The vocoder of claim 1, wherein said electrical pulses are low curent level square wave pulses of alternating polarity and of adjustable pulse width and pulse rate with equal but opposite current in each of said pulses, and a predetermined period between pairs of said pulses in which there is no current flow.

3. The vocoder of claim 2, wherein said means for converting said input signal into control signals includes:
    means for estimating the frequency of the fundamental voicing component of said speech signal;
    means for estimating the amplitude and the frequency of at least one formant component of said speech signal;
    programmable means which in use causes the application of said electrical pulses to selected ones of said electrode means, said programmable means being programmed with data defining a predetermined relationship between each said electrode and a selected range of said estimated formant frequency components, and for causing selection of said electrode on the basis of said predetermined relationship, said programmable means being programmed such that at least one formant frequency component is the second formant frequency component of said speech signal in the range 0 Hz to 6000 Hz;
    said programmable means further being programmed to control said current pulses on the basis of said estimated amplitude of said formant frequency component, the width of each of said current pulses being a function of said estimated amplitude, and on the basis of predetermined data relating to the sensitivity of the hearing impaired person to stimulation of the digital nerve bundles underlying each said electrode;
    said programmable means further being programmed to control the extent of application of said current pulses to said selected electrodes, said current pulses being applied at a frequency which is related linearly to the estimated frequency of said fundamental voicing component.

4. The vocoder of claim 3, wherein said predetermined relationship between each finger electrode and a selected range of said estimated formant frequency components is such that each adjacent electrode covers an increasing range of said estimated formant frequency components proceeding from the finger at one side of the hand to the other.

5. The vocoder of claim 3, wherein the electrodes applied to the index finger cover the lowest frequency range while the electrodes applied to the fourth finger cover the highest frequency range.

6. The vocoder of claim 5, wherein said predetermined relationship between said selected range of said estimated formant frequency component and the electrodes applied to the fingers of the hand are in accordance with the following table:

| Electrode 1 Index finger | about | 0.900 Hz; |  |
|---|---|---|---|
| Electrode 2 Index finger | " | 900–1100 Hz; |  |
| Electrode 3 Second finger | " | 1100–1300 Hz; |  |
| Electrode 4 Second finger | " | 1300–1500 Hz; |  |
| Electrode 5 Third finger | " | 1500–1700 Hz; |  |
| Electrode 6 Third finger | " | 1700–2400 Hz; |  |
| Electrode 7 Fourth finger | " | 2400–3300 Hz; | and |
| Electrode 8 Fourth finger | " | 3300–4000 Hz. |  |

* * * * *